United States Patent
Morita et al.

(10) Patent No.: US 8,828,369 B2
(45) Date of Patent: *Sep. 9, 2014

(54) LIQUID COSMETIC

(75) Inventors: Masaaki Morita, Fujioka (JP); Hiroshi Sato, Fujioka (JP)

(73) Assignee: Mitsubishi Pencil Co., Ltd., Shinagawa-ku, Tokyo (JP)

( * ) Notice: Subject to any disclaimer, the term of this patent is extended or adjusted under 35 U.S.C. 154(b) by 589 days.

This patent is subject to a terminal disclaimer.

(21) Appl. No.: 12/161,492

(22) PCT Filed: Jan. 19, 2007

(86) PCT No.: PCT/JP2007/050813
§ 371 (c)(1),
(2), (4) Date: Jul. 18, 2008

(87) PCT Pub. No.: WO2007/083753
PCT Pub. Date: Jul. 26, 2007

(65) Prior Publication Data
US 2010/0221204 A1  Sep. 2, 2010

(30) Foreign Application Priority Data
Jan. 20, 2006  (JP) ................. 2006-012874

(51) Int. Cl.
*A61K 8/81* (2006.01)
(52) U.S. Cl.
USPC ..................... 424/70.16; 424/70.17; 424/401
(58) Field of Classification Search
USPC ................... 424/70.16, 70.17, 401
See application file for complete search history.

(56) References Cited

U.S. PATENT DOCUMENTS

| 3,639,572 A | 2/1972 | Heinrich et al. |
| 2005/0163741 A1 | 7/2005 | Zech |

FOREIGN PATENT DOCUMENTS

| EP | 1 010 420 A1 | 6/2000 |
| JP | 2-12924 B2 | 3/1990 |
| JP | 4-66447 B2 | 10/1992 |
| JP | 7-47529 B2 | 5/1995 |
| JP | 10-231233 A | 9/1998 |
| JP | 2000-247833 A | 9/2000 |
| JP | 2002-241233 A | 8/2002 |
| JP | 2003-73220 A | 3/2003 |
| JP | 2003-231614 A | 8/2003 |
| JP | 2004-175709 A | 6/2004 |

OTHER PUBLICATIONS

Liquid eyeliner, Retrieved online [Jan. 21, 2013], Retrieved from URL:<http://www.thebodyshop.com/make-up/eyes/liquid-eyeliner.aspx>.*
Notification of Transmittal of Translation of the International Preliminary Report on Patentability (Form PCT/IB/338), International Preliminary Report on Patentability (Form PCT/IB/373), Written Opinion of the International Search Authority (Form PCT/ISA/237) mailed in corresponding International Patent Application No. PCT/JP2007/050813, Jul. 31, 2008, The International Bureau of WIPO, Geneva, CH.
Extended Search Report from European Patent Office issued in corresponding European Patent Application No. 07707101.7 dated Nov. 23, 2010.
International Search Report (PCT/ISA/210), Feb. 27, 2007.

* cited by examiner

*Primary Examiner* — Lezah Roberts
*Assistant Examiner* — Nannette Holloman
(74) *Attorney, Agent, or Firm* — Buchanan, Ingersoll & Rooney PC

(57) ABSTRACT

Provided is a liquid cosmetic comprising at least an inorganic pigment, a dispersant, a film forming agent and water, wherein the dispersant is a homopolymer or a copolymer obtained by polymerizing a raw material monomer of at least one compound selected from acrylic acid, methacrylic acid or ($C_1$ to $C_4$ and $C_8$) alkyl esters thereof, and the film forming agent comprises an emulsion of a homopolymer (excluding a homopolymer comprising only polystyrene) or a copolymer obtained by polymerizing a raw material monomer of at least one compound selected from acrylic acid, methacrylic acid, ($C_1$ to $C_4$ and $C_8$) alkyl esters thereof or styrene.

5 Claims, No Drawings

LIQUID COSMETIC

TECHNICAL FIELD

The present invention relates to a liquid cosmetic, specifically to an aqueous liquid cosmetic. To be more specific, the present invention relates to a liquid cosmetic suited to cosmetic uses in which the cosmetic is filled into a vessel for a liquid cosmetic applicator and coated by using a brush-like coating part, wherein it is excellent in water resistance and skin adhesiveness.

BACKGROUND ART

Cosmetics in which dyes as a colorant are dissolved in water and water-soluble organic solvents and cosmetics in which pigments are dispersed in water and water-soluble organic solvents together with surfactants and water-soluble resins have so far been known as a liquid cosmetic of a type in which it is used with being stored in an applicator. When dyes are used for the liquid cosmetics, lines drawn by these liquid cosmetics are usually poor in durability. Accordingly, a pigment as a colorant and a surfactant as a dispersant are used, and a water-soluble resin is blended into the liquid cosmetics, whereby dispersibility and an adhesive property of the pigment are improved to uniformize color density of lines drawn by the liquid cosmetics and to enhance water resistance thereof.

Patent document 1, patent document 2 and patent document 3 relate to patent applications applied by the present applicant, and they provide eye makeup cosmetics comprising aqueous dispersions and liquid cosmetic applicators in which the above eye makeup cosmetics are stored in applicator vessels. The cosmetics disclosed in the above documents are excellent in a coating performance and provide satisfactory drawn lines. The cosmetics disclosed in the documents are preferred from the viewpoints that they contain lecithin and nonionic surfactants in large amounts and that they can completely be wiped with wet tissue. In contrary to this, however, they have a defect that they are inferior particularly in a water resistant adhesive performance.

Patent document 4 relates as well to patent application applied by the present applicant, and a liquid cosmetic applicator in which a liquid eyeliner cosmetic prepared by using particularly a pearl pigment is stored is provided therein. In the liquid cosmetic applicator, a fine eyeliner liquid is filled, wherein in order to stabilize the liquid, a viscosity at a specific shear rate is set to a prescribed numerical range, and hydrogenated lecithin, polyethylene glycol fatty acid esters and the like are used as a dispersion stabilizer. The liquid cosmetics disclosed above make it possible to draw fine eyelines, but involved therein is a defect that they are inferior in a water resistant adhesive performance because of the reasons that large particles are used and that 0.5% of hydrogenated lecithin and 0.5% of a polyethylene glycol fatty acid ester are added as stabilizing agents.

A liquid cosmetic characterized by comprising a pigment, water, a water-soluble polymer and glycols and having a viscosity of 1 to 50 mPa·s is disclosed in patent document 5. However, an emulsion and the like can not be added in the liquid cosmetic for achieving the above low viscosity, and it is easily presumed that defects are found in ooze resistance and water resistance due to the low viscosity.

An eyeliner cosmetic in which an inorganic pigment is dispersed by polyasparagic acid, polyglutamic acid and salts thereof and which is further blended with a polymer emulsion is disclosed in patent document 6. It is described herein that the eyeliner cosmetic has good dispersibility. However, it is presumed that it is difficult to provide the eyeliner cosmetic with ooze resistance and strong water resistance because of the reasons that the eyeliner cosmetic is blended with a large amount of a polyasparagic acid salt, which is an anionic surfactant, as a dispersant and that it is a cosmetic in which a viscosity of the liquid is controlled to a low level. In this respect, the same shall apply to patent document 7.

A liquid cosmetic described in patent document 8 has a viscosity value falling in a low viscosity range, and in such a liquid cosmetic containing an inorganic pigment as a component, almost all of inorganic pigments having a high specific gravity settle down quickly, so that it does not suit to actual use. Further, in the liquid cosmetic disclosed in patent document 8, the dispersant contained therein is restricted to a betaine type amphoteric resin, and therefore the water resistance is not necessarily satisfactory.

Patent document 1: Japanese Patent Publication No, 12924/1990
Patent document 2: Japanese Patent Publication No 66447/1992
Patent document 3: Japanese Patent Application Laid-Open No. 231233/1998
Patent document 4: Japanese Patent Application Laid-Open Na 247833/2000
Patent document 5: Japanese Patent Publication No. 47529/1995
Patent document 6: Japanese Patent Application Laid-Open No. 175709/2004
Patent document 7: Japanese Patent Application Laid-Open Na 231614/2003
Patent document 8: Japanese Patent Application Laid-Open No, 73220/2003

DISCLOSURE OF THE INVENTION

Problem to be Solved by the Invention

As described above, conventional liquid cosmetics prepared by using pigments as a colorant and adding water-soluble resins for fixing and conventional liquid cosmetics prepared by using water-soluble resins as a dispersant have had the problems that they have an unsatisfactory water resistance and that when sweating, the make-up deteriorates gradually and the cosmetic is lost. An object of the present invention is to provide a liquid cosmetic in which the foregoing problems on prior art are overcome and which is excellent in water resistance.

Means for Solving Problem

The present invention relates to a liquid cosmetic comprising at least an inorganic pigment, a dispersant, a film forming agent and water, wherein the dispersant is a homopolymer or a copolymer obtained by polymerizing a raw material monomer of at least one compound selected from acrylic acid, methacrylic acid or ($C_1$ to $C_4$ and $C_8$) alkyl esters thereof, and the film forming agent comprises an emulsion of a homopolymer (excluding a homopolymer comprising only polystyrene) or a copolymer obtained by polymerizing a raw material monomer of at least one compound selected from acrylic acid, methacrylic acid, ($C_1$ to $C_4$ and $C_8$) alkyl esters thereof or styrene.

Effect of the Invention

The liquid cosmetic of the present invention is a liquid cosmetic suited to cosmetic uses in which the cosmetic is filled into a vessel for a liquid cosmetic applicator and coated by a brush-like coating part, and it is excellent in all of water resistance, skin adhesiveness, settling stability and a coating property.

BEST MODE FOR CARRYING OUT THE INVENTION

The liquid cosmetic of the present invention shall be explained below in details.

In the liquid cosmetic of the present invention, the dispersant is a homopolymer or a copolymer obtained by polymerizing a raw material monomer of at least one compound selected from acrylic acid, methacrylic acid or ($C_1$ to $C_4$ and $C_8$) alkyl esters thereof. The homopolymer or the copolymer is preferably an acryl resin which has an acid residue as a side chain in a repetitive structure thereof and which can be dissolved in water by neutralization. A copolymer (formula shown below) of a mixture comprising tert-butyl acrylate, ethyl acrylate and methacrylic acid shall be exemplified as the particularly desired acryl resin. To be specific, it includes, for example, Luvimer 100P manufactured by BASF AG and the like.

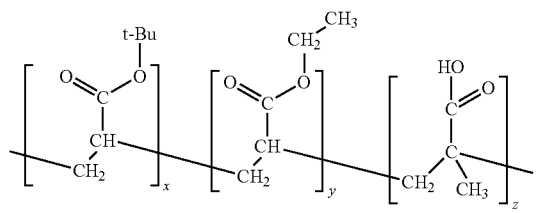

In dissolving the acryl resin in water by neutralization, capable of being suitably used are organic basic compounds such as 2-amino-2-methyl-1-propanol, 2-amino-2-methyl-1, 3-propanediol, L-arginine and the like which can be paired with free organic acid residues having bulky organic groups to form salts and inorganic basic compounds such as aqueous ammonia, sodium hydroxide and the like. Among them, the particularly preferred basic compound is 2-amino-2-methyl-1-propanol.

In the liquid cosmetic of the present invention, the basic compounds are reacted with the homopolymer or copolymer described above to form a polymer structure having a salt, and then a minimum amount of purified water required for dissolving the polymer is added to prepare an aqueous solution which is used as the above dispersant.

In this regard, the above polymer of an acryl resin base used as the dispersant in the liquid cosmetic of the present invention is a polymer which is different in a structure from a betaine type acryl acid base amphoteric resin used as the dispersant for a pigment in a liquid cosmetic described in Japanese Patent Application Laid-Open No. 73220/2003.

In the liquid cosmetic of the present invention, a blend amount of the dispersant is preferably 0.5 to 5 mass %, more preferably 2 to 4 mass % based on the total amount of the liquid cosmetic. If it is less than 0.5 mass %, dispersion stability of the pigment is unsatisfactory. On the other hand, if the dispersant is added in excess of 5 mass %, the viscosity becomes too high, and the dispersion stability is not much improved, so that it is not economical.

The film forming agent means an emulsion of a homopolymer (excluding a homopolymer comprising only polystyrene) or a copolymer obtained by polymerizing the raw material monomer of at least one compound selected from acrylic acid, methacrylic acid or ($C_1$ to $C_4$ and $C_8$) alkyl esters thereof and styrene (aqueous suspension obtained by emulsion-polymerizing the monomer in water of a polymerization solvent in the case of either the homopolymer or the copolymer).

In the present invention, an emulsion of a homopolymer or a copolymer obtained by polymerizing at least one monomer selected from acrylic acid, methacrylic acid or ($C_1$ to $C_4$ and $C_8$) alkyl esters thereof can be used as the emulsion of the above film forming agent. To be specific, Yodosol GH800 manufactured by Nippon NSC Ltd., COVACRYL MS11 manufactured by Daito Kasei Kogyo Co., Ltd. and the like can be used. A blend amount of the emulsion is preferably 2 to 15 mass % in terms of solid content based on the total amount of the liquid cosmetic. If it is less than 2 mass %, the water resistance is inferior, and if it exceeds 15 mass %, a coating part of the applicator is dried to likely become impossible in coating.

A surfactant is used in the emulsion of the film forming agent in a certain case in order to stabilize the emulsion itself. In this connection, an addition amount of the surfactant shall not specifically be restricted since it exerts less effect on the water resistance and the skin adhesiveness which are features of the liquid cosmetic of the present invention. The reason for exerting less effect on the water resistance and the skin adhesiveness is speculated to be attributable to the fact that the surfactant is present probably in a free state and less liable to bring about electrostatic or stereoelectronic interaction with the emulsion.

In the present invention, capable of being suitably used as the inorganic pigment are oxides such as titanium oxide, zinc oxide, red iron oxide, chromium oxide, black iron oxide, yellow iron oxide and the like, titan black, lithium cobalt titanate, sintered pigments such as titan-titanium oxide sintered products and the like and pigments such as Prussian blue, ultramarine blue, carbon black and the like. The primary particle diameter is about 0.2 to 1 µm in the case of, for example, black iron oxide and about 0.02 to 0.7 µm in the case of red iron oxide. The liquid cosmetic of the present invention containing the above pigments has a large specific gravity, and the specific gravity thereof falls, though depending on an amount of the pigment contained, in a range of about 1 to 1.4 when prepared as a liquid cosmetic for an eyeliner. In the liquid cosmetic of the present invention, a blend amount of the inorganic pigment falls in a range of preferably 1 to 30 mass %, more preferably 5 to 25 mass % based on the total amount of the liquid cosmetic. If it is less than 1 mass %, the color development is weak and insufficient for a cosmetic. If the inorganic pigment is added in excess of 30 mass %, the color development is not improved so much as corresponding thereto, and the production cost is increased, so that it is lacking in economical efficiency.

In the present invention, any kind of surfactants of a nonionic base, a cationic base and an anionic base can be used as the surfactant. To be specific, they include lecithin, propylene glycol fatty acid esters, glycerin fatty acid esters, polyglycerin fatty acid esters, polyoxyethylene alkyl ethers, polyoxyethylene polyoxypropylene alkyl ethers, polyoxyethylene alkyl ether phosphates (phosphoric esters), polyethylene glycol fatty acid ester-alkyl sulfate (sulfonic esters), polyoxyethylene alkyl ether sulfates and the like.

An amount of the surfactant is preferably 0.5 mass % or less based on the total amount of the liquid cosmetic. If it is added in excess of 0.5 mass %, the water resistance is inferior, and the satisfactory adhesive strength can not be obtained.

Viscosity Value of the Liquid Cosmetic:

A viscosity value (25° C.) of the liquid cosmetic of the present invention falls in a range of 50 to 200 mPa·s, preferably 80 to 150 mPa·s. The viscosity value is a value measured by means of an EMD type viscometer manufactured by Tokimec Inc. with a standard cone rotor of 20 rpm (shear rate: 76.8 s$^{-1}$). If a viscosity value of the liquid cosmetic is less than 50 mPa·s, settling of the solid components is caused with the passage of time, so that the situations may occur that the liquid cosmetic filled into an applicator can not evenly be coated and that lumps are produced in the applicator to make coating impossible. Accordingly, that is not preferred. On the other hand, if a viscosity value of the liquid cosmetic exceeds 200 mPa·s, the liquid cosmetic filled into the applicator is lacking in followability in coating due to the high viscosity, and therefore it is difficult in a certain case to coat smoothly the liquid cosmetic. Accordingly, that is not preferred.

In Japanese Patent Application Laid-Open No. 73220/2003 (patent document 8), the viscosity value is measured by means of the ELD type viscometer manufactured by Tokimec Inc. with a standard cone rotor of 10 rpm, that is, at a shear rate of 38.3 s$^{-1}$ for the viscosity value of less than 50 mPa·s and with a standard cone rotor of 1 rpm, that is, at a shear rate of 3.83 s$^{-1}$ for the viscosity value of 50 mPa·s or more and less than 600 mPa·s.

When a viscosity value of the liquid cosmetic of the present invention was measured at a shear rate of 3.83 s$^{-1}$, which was one of the viscosity value measuring conditions used in the patent document 8, the result that the viscosity value was 400 to 2000 mPa·s was obtained. As shown above, a viscosity value of the liquid cosmetic of the present invention is larger by several ten to several hundred times as compared with that of the liquid cosmetic described in the patent document 8.

The viscosity values (mPa·s) of the liquid cosmetic of the present invention and the liquid cosmetic described in the patent document 8 at the respective shear rates are shown in Table 1 for comparison.

TABLE 1

| Shear rate (s$^{-1}$) | Patent document 8 | Present invention |
|---|---|---|
| 3.83 | 50 to 300 | 400 to 2000 |
| 38.3 | 1 to 50 | |
| 76.8 | | 50 to 200 | unit: mPa · s

As described above, if the viscosity value at a shear rate of 3.83 s$^{-1}$ is smaller than 400 mPa·s, brought about are the disadvantages that a settling speed of the inorganic pigment and the like contained in the liquid cosmetic is increased to allow the particles settled with the passage of time during storing to be turned into a hard cake and that it is difficult to evenly disperse again the hard cake. On the other hand, if the viscosity value at a shear rate of 3.83 s$^{-1}$ is larger than 2000 mPa·s, settling of the inorganic pigment and the like contained in the liquid cosmetic is inhibited, but the disadvantage that the coating feeling is deteriorated is involved therein.

In contrast with this, the liquid cosmetic of the present invention is notably different from the liquid cosmetic described in patent document 8 in that an inorganic pigment which is excellent in water resistance and has a high specific gravity can suitably be used with controlling the viscosity to the prescribed range described above.

Coating Performance of the Liquid Cosmetic:

The liquid cosmetic of the present invention is a liquid cosmetic comprising at least an inorganic pigment, a dispersant, a film forming agent and water, and is characterized in that it is further blended, if necessary, with a surfactant. In this respect, the dispersant means a material obtained by reacting a basic compound with a homopolymer or a copolymer polymerizing a raw material monomer of at least one compound selected from acrylic acid, methacrylic acid or ($C_1$ to $C_4$ and $C_8$) alkyl esters thereof to form a salt structure and turning it into an aqueous solution. Further, the film forming agent means an emulsion of a homopolymer (excluding a homopolymer comprising only polystyrene) or a copolymer obtained by polymerizing a raw material monomer of at least one compound selected from acrylic acid, methacrylic acid or ($C_1$ to $C_4$ and $C_8$) alkyl esters thereof and styrene (aqueous suspension obtained by emulsion-polymerizing the monomer in water of a polymerization solvent in the case of either the homopolymer or the copolymer). The liquid cosmetic of the present invention comprising the constitution described above is very excellent in a water resistant adhesive property and makes it easy to draw fine lines. Accordingly, it can suitably be used for makeup cosmetics such as an eyeliner, an eyebrow and the like.

EXAMPLES

The present invention shall be explained below in further details with reference to examples.

The viscosities of the respective liquid cosmetics prepared in the examples and the comparative examples were measured by means of an EMD type viscometer manufactured by Tokimec Inc. with a standard cone rotor of 20 rpm (shear rate: 76.8 s$^{-1}$) at a measuring temperature of 25° C. Hereinafter, a term shown merely by "part" means "mass part".

Example 1

| | |
|---|---|
| Black iron oxide | 10.0 parts |
| Alkyl acrylate copolymer | 0.6 part |
| Alkyl acrylate copolymer emulsion | 20.0 parts |
| (Resin content in the emulsion) | 9.0 parts |
| Disodium edetate | 0.3 part |
| 1,3-Butylene glycol | 8.0 parts |
| Xanthan gum | 0.3 part |
| Methyl paraben | 0.4 part |
| Sodium dehydroacetate | 0.1 part |
| Purified water | balance |
| | (51.3 parts) |
| Total | 100.0 parts |

The components described above were mixed and stirred at room temperature for 3 hours to obtain a black liquid cosmetic having a viscosity of 84 mPa·s. The liquid cosmetic thus obtained had excellent properties in all of an adhesive property, a settling property and a coating property.

Liquid cosmetics were produced in the respective formulation shown in Table 2 and Table 3 in the same manner as in Example 1, and the respective liquid cosmetics in the examples of the present invention and the comparative examples were measured for viscosities and evaluated according to criteria shown below to obtain results shown in Table 2 and Table 3.

A blend amount of the dispersant shown in Table 2 and Table 3 is shown in terms of the resin content (mass % based on the total amount of the liquid cosmetic) contained in the dispersant used.

TABLE 2

| Components | Compound name | Example 1 | 2 | 3 | 4 | 5 |
|---|---|---|---|---|---|---|
| Pigment | Black iron oxide | 10 | 10 | 10 | 0 | 0 |
| Pigment | Iron oxide-coated titanium oxide-coated mica | 0 | 0 | 0 | 10 | 10 |
| Dispersant | Alkyl acrylate copolymer*1 | 0.6 | 3 | 4.5 | 3 | 4.5 |
| Surfactant | Polyoxyethylene alkyl(C12 to C15) ether phosphate (10 E.O.) | 0 | 0 | 0 | 0.3 | 0 |
| Surfactant | Polyethylene glycol monostearate | 0 | 0 | 0 | 0 | 0.5 |
| Film forming agent emulsion (resin content in the emulsion) | Alkyl acrylate copolymer emulsion*2 | 20 / 9 | 15 / 6.75 | 10 / 4.5 | 15 / 6.75 | 10 / 4.5 |
| Chelating agent | Disodium edetate | 0.3 | 0.3 | 0.3 | 0.3 | 0.3 |
| Moisturizing agent | 1,3-Butylene glycol | 8 | 8 | 8 | 8 | 8 |
| Thickener | Xanthan gum | 0.3 | 0.25 | 0.5 | 0.5 | 0.6 |
| Antiseptic agent | Methyl paraben | 0.4 | 0.4 | 0.4 | 0.4 | 0.4 |
| Antiseptic agent | Sodium dehydroacetate | 0.1 | 0.1 | 0.1 | 0.1 | 0.1 |
| Purified water | | balance | balance | balance | balance | balance |
| Evaluation | | | | | | |
| Viscosity (mPa·s) | Viscosity measuring condition: | | | | | |
| | shear rate 76.8 (1/s) | 84 | 55 | 145 | 136 | 180 |
| | shear rate 3.83 (1/s) | 780 | 510 | 1346 | 1263 | 1671 |
| Adhesive property | | ○ | ◎ | ◎ | ○ | ○ |
| Settling property | | ○ | ○ | ○ | ○ | ○ |
| Coating feeling | | ◎ | ◎ | ◎ | ◎ | ◎ |

*1 Alkyl acrylate copolymer: Luvimer 100P manufactured by BASF AG.
*2 Alkyl acrylate copolymer emulsion: Yodosol GH800 manufactured by Nippon NSC Ltd.

TABLE 3

| Components | Compound name | Comparative example 1 | 2 | 3 | 4 | 5 | 6 | 7 |
|---|---|---|---|---|---|---|---|---|
| Pigment | Black iron oxide | 10 | 10 | 10 | 10 | 0 | 0 | 10 |
| Pigment | Iron oxide-coated titanium oxide-coated mica | 0 | 0 | 0 | 0 | 10 | 10 | 0 |
| Dispersant | Alkyl acrylate copolymer*1 | 3 | 3 | 3 | 0 | 3 | 3 | 0 |
| Dispersant | *2 | | | | | | | |
| Surfactant | Polyoxyethylene alkyl (C12 to C15) ether phosphate (10 E.O.) | 1.5 | 1 | 0.5 | 0.5 | 0 | 0 | 0 |
| Surfactant | Polyethylene glycol monostearate | 0 | 0 | 0 | 0 | 0.3 | 0.5 | 0 |
| Film forming agent emulsion (resin content in the emulsion) | Alkyl acrylate copolymer emulsion*3 | 20 / 9 | 20 / 9 | 0 / 0 | 10 / 4.5 | 15 / 6.75 | 15 / 6.75 | 15 / 6.75 |
| Chelating agent | Disodium edetate | 0.3 | 0.3 | 0.3 | 0.3 | 0.3 | 0.3 | 0.3 |
| Moisturizing agent | 1,3-Butylene glycol | 8 | 8 | 8 | 8 | 8 | 8 | 8 |
| Thickener | Xanthan gum | 0.5 | 0.25 | 0.5 | 0.5 | 0.1 | 0.7 | 0.2 |
| Antiseptic agent | Methyl paraben | 0.4 | 0.4 | 0.4 | 0.4 | 0.4 | 0.4 | 0.4 |
| Antiseptic agent | Sodium dehydroacetate | 0.1 | 0.1 | 0.1 | 0.1 | 0.1 | 0.1 | 0.1 |
| Purified water | | balance | balance | balance | balance | balance | balance | balance |
| Evaluation | | | | | | | | |
| Viscosity (mPa·s) | Viscosity measuring condition: | | | | | | | |
| | shear rate 76.8 (1/s) | 136 | 54 | 130 | 130 | 40 | 230 | 53 |
| | shear rate 3.83 (1/s) | 1251 | 498 | 1207 | 1203 | 371 | 2135 | 492 |
| Adhesive property | | X | Δ | X | X | ○ | ○ | X |
| Settling property | | ○ | Δ | ○ | ○ | X | ○ | ○ |
| Coating feeling | | ○ | ○ | ○ | ○ | Δ | X | ○ |

*1 Alkyl acrylate copolymer Luvimer 100P manufactured by BASF AG.
*2 N-methacryloyloxyethyl-N,N-dimethylammonium-α-N-methylcarboxybetaine•alkyl methacrylate copolymer liquid (betaine type alkyl acid base amphoteric resin)
*3 Alkyl acrylate copolymer emulsion Yodosol GH800 manufactured by Nippon NSC Ltd.

Evaluation Criteria:
Evaluation of Adhesive Property

The adhesive property was sensuously evaluated by coating the liquid cosmetic on a back of a hand, naturally drying it for 10 minutes, then applying flowing water on the coated part, rubbing it with a finger and observing with eyes and feeling with a finger tip whether the coated cosmetic was removed.

⊚: no peeling on the coated part and very good
○: less peeling on the coated part and good
Δ: partial peeling on the coated part
X: peeling on almost all of the coated part Evaluation of Settling Property The settling property was evaluated by filling a pen type vessel for coating a liquid cosmetic with the liquid cosmetics obtained in the examples and the comparative examples described above, leaving the vessel vertically standing still for a month and then observing the state of the liquid cosmetic filled in the coating vessel with eyes.

In evaluating the settling property, a case in which the liquid cosmetic filled in the vessel did not bring about phase separation was classified to an excellent settling property;

a case in which phase separation was caused but a transparent liquid layer produced as a supernatant on an upper part of the liquid cosmetic in the vessel had a thickness of less than 2 mm was classified to a good settling property;

a case in which color separation and phase separation were observed a little in the liquid cosmetic filled in the vessel and in which it could be used without problems by shaking very slightly the vessel before use was classified to an average settling property; and a case in which color separation and phase separation were obviously observed in the liquid cosmetic filled in the vessel to bring about unevenness of a color and intensity even after shaking the vessel to some extent before use and in which the cosmetic was not suited to actual use was classified to an inferior settling property.

⊚: no phase separation was caused
○: separated layer produced as a supernatant on an upper part of the cosmetic filled in the vessel had a thickness of less than 2 mm
Δ: color separation and phase separation were observed a little in the cosmetic filled in the vessel, but it could be used without problems by shaking slightly the vessel before use
X: color separation and phase separation were observed in the cosmetic filled in the vessel, and unevenness of intensity caused was not improved after shaking the vessel to some extent, so that the cosmetic was not suited to actual use Evaluation of Coating Property The respective liquid cosmetics obtained in the examples and the comparative examples described above were actually used by twenty female panellers having makeup experience of five years or longer to sensuously evaluate use feeling (smoothness, stickiness and the like) in coating.

⊚: 15 persons or more out of the twenty panellers answered that the use feeling was good
○: 10 persons or more and 14 persons or less out of the twenty panellers answered that the use feeling was good
Δ: 6 persons or more and 9 persons or less out of the twenty panellers answered that the use feeling was good
X: only 5 persons or less out of the twenty panellers answered that the use feeling was good Yukaformer manufactured by Mitsubishi Chemical Corporation which is a betaine type acrylic acid base amphoteric resin used as a pigment dispersant in Japanese Patent Application Laid-Open No. 73220/2003 (patent document 8) was used as the dispersant in Comparative Example 7 in place of the dispersant used in the liquid cosmetic of the present invention. As apparent from the result thereof, when the above betaine type acrylic acid base amphoteric resin was used as the dispersant in the present invention, the evaluation result of the adhesive property was not good.

Industrial Applicability

Provided by the present invention is an aqueous liquid cosmetic which is excellent in water resistance and skin adhesiveness, wherein it is suited to cosmetic uses in which the cosmetic is filled into a vessel for a liquid cosmetic applicator and coated by using a brush-like coating part. The liquid cosmetic of the present invention is water-soluble, but excellent in water resistance and ooze resistance, and in addition thereto, it is excellent in an adhesive property as well as a settling property of a pigment and coating feeling. Due to easiness and comfortable feeling in use, the liquid cosmetic of the present invention has a high utility value in terms of actual use for a cosmetic.

What is claimed is:

1. A liquid cosmetic comprising at least an inorganic pigment, a dispersant, a film forming agent, a chelating agent and water, wherein the dispersant is an aqueous solution of a copolymer which is a copolymer of a mixture comprising tert-butyl acrylate, ethyl acrylate and methacrylic acid and which assumes a salt structure with a basic compound, and the film forming agent is an emulsion of a homopolymer obtained by polymerizing a raw material monomer selected from acrylic acid, methacrylic acid, or ($C_1$ to $C_4$ and $C_8$) alkyl esters thereof, or an emulsion of a copolymer obtained by polymerizing raw materials monomers of at least two compounds selected from acrylic acid, methacrylic acid, ($C_1$ to $C_4$ and $C_8$) alkyl esters thereof and styrene, and wherein the liquid cosmetic further comprises no surfactant or 0.5 mass % or less of a surfactant and has a viscosity of 50 to 200 mPa·s at 25° C. and a shear rate of 76.8 $s^{-1}$.

2. The liquid cosmetic as described in claim 1, wherein a blend amount of the dispersant is 0.5 to 5 mass % based on the total amount of the liquid cosmetic.

3. The liquid cosmetic as described in claim 1, wherein a blend amount of the film forming agent is 2 to 15 mass % in terms of a solid content based on the total amount of the liquid cosmetic.

4. An applicator for an eyeliner filled with the liquid cosmetic as described in claim 1.

5. An applicator for an eyebrow cosmetic filled with the liquid cosmetic as described in claim 1.

* * * * *